US011974804B2

(12) United States Patent
Zarins et al.

(10) Patent No.: US 11,974,804 B2
(45) Date of Patent: May 7, 2024

(54) BILATERAL RENAL NEUROMODULATION

(71) Applicant: Medtronic Ireland Manufacturing Unlimited Company, Dublin (IE)

(72) Inventors: Denise Zarins, Los Gatos, CA (US); Hanson Gifford, III, Woodside, CA (US); Mark E. Deem, Mountain View, CA (US); Douglas Sutton, Pacifica, CA (US); Howard R. Levin, Teaneck, NJ (US); Mark Gelfand, New York, NY (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 337 days.

(21) Appl. No.: 17/365,868

(22) Filed: Jul. 1, 2021

(65) Prior Publication Data

US 2021/0330378 A1 Oct. 28, 2021

Related U.S. Application Data

(63) Continuation of application No. 16/211,164, filed on Dec. 5, 2018, now abandoned, which is a continuation
(Continued)

(51) Int. Cl.
*A61B 18/14* (2006.01)
*A61B 18/00* (2006.01)
(Continued)

(52) U.S. Cl.
CPC ............ *A61B 18/1492* (2013.01); *A61F 7/12* (2013.01); *A61M 5/14276* (2013.01); *A61N 1/05* (2013.01);
(Continued)

(58) Field of Classification Search
CPC ........ A61B 18/1492; A61B 2018/0022; A61B 2018/00267; A61B 2018/00434; A61B 2018/00511; A61B 2018/00577; A61B 2018/00613; A61N 1/327; A61N 1/36017; A61N 1/36117; A61N 1/36121; A61N 7/02; A61N 2007/003; A61N 2007/025; A61M 5/14276; A61M 2210/1082
See application file for complete search history.

(56) References Cited

U.S. PATENT DOCUMENTS 7,551,057 B2 6/2009 King et al.
8,145,316 B2 3/2012 Deem et al.
10,034,708 B2 7/2018 Zarins et al.

*Primary Examiner* — Mark W. Bockelman
(74) *Attorney, Agent, or Firm* — Shumaker & Sieffert, P.A.

(57) ABSTRACT

Methods and apparatus are provided for treating hypertension, e.g., via a pulsed electric field, via a stimulation electric field, via localized drug delivery, via high frequency ultrasound, via thermal techniques, etc. Such neuromodulation may effectuate irreversible electroporation or electrofusion, necrosis and/or inducement of apoptosis, alteration of gene expression, action potential attenuation or blockade, changes in cytokine up-regulation and other conditions in target neural fibers. In some embodiments, neuromodulation is applied to neural fibers that contribute to renal function. In some embodiments, such neuromodulation is performed in a bilateral fashion. Bilateral renal neuromodulation may provide enhanced therapeutic effect in some patients as compared to renal neuromodulation performed unilaterally, i.e., as compared to renal neuromodulation performed on neural tissue innervating a single kidney.

19 Claims, 10 Drawing Sheets

Related U.S. Application Data of application No. 15/862,452, filed on Jan. 4, 2018, now Pat. No. 10,179,027, which is a continuation of application No. 15/466,594, filed on Mar. 22, 2017, now Pat. No. 9,895,195, which is a continuation of application No. 15/059,332, filed on Mar. 3, 2016, now Pat. No. 9,636,174, which is a continuation of application No. 14/549,229, filed on Nov. 20, 2014, now Pat. No. 9,308,044, which is a continuation of application No. 14/285,217, filed on May 22, 2014, now abandoned, which is a continuation of application No. 13/361,620, filed on Jan. 30, 2012, now abandoned, which is a continuation of application No. 11/368,577, filed on Mar. 6, 2006, now Pat. No. 8,145,317.

(51) Int. Cl.

| | | |
|---|---|---|
| *A61F 7/12* | (2006.01) | |
| *A61M 5/142* | (2006.01) | |
| *A61N 1/05* | (2006.01) | |
| *A61N 1/32* | (2006.01) | |
| *A61N 1/36* | (2006.01) | |
| *A61N 7/00* | (2006.01) | |
| *A61N 7/02* | (2006.01) | |

(52) U.S. Cl.
CPC ......... *A61N 1/327* (2013.01); *A61N 1/36017* (2013.01); *A61N 1/36117* (2013.01); *A61N 1/36121* (2013.01); *A61N 7/00* (2013.01); *A61N 7/02* (2013.01); *A61B 2018/0022* (2013.01); *A61B 2018/00267* (2013.01); *A61B 2018/00351* (2013.01); *A61B 2018/00404* (2013.01); *A61B 2018/00434* (2013.01); *A61B 2018/00511* (2013.01); *A61B 2018/00577* (2013.01); *A61B 2018/00613* (2013.01); *A61F 2007/126* (2013.01); *A61M 2210/1082* (2013.01); *A61M 2210/12* (2013.01); *A61N 1/36114* (2013.01); *A61N 2007/0021* (2013.01); *A61N 2007/003* (2013.01); *A61N 2007/025* (2013.01)

BILATERAL RENAL NEUROMODULATION

CROSS-REFERENCE TO RELATED APPLICATIONS

This application is a continuation of U.S. patent application Ser. No. 16/211,164, filed Dec. 5, 2018, which is a continuation of U.S. patent Ser. No. 15/862,452, filed Jan. 4, 2018, now U.S. Pat. No. 10,179,027, which is a continuation of U.S. patent application Ser. No. 15/466,594, filed Mar. 22, 2017, now U.S. Pat. No. 9,895,195, which is a continuation of U.S. patent application Ser. No. 15/059,332, filed Mar. 3, 2016, now U.S. Pat. No. 9,636,174, which is a continuation of U.S. patent application Ser. No. 14/549,229, filed Nov. 20, 2014, now U.S. Pat. No. 9,308,044, which is a continuation of U.S. patent application Ser. No. 14/285,217, filed May 22, 2014, now abandoned, which is a continuation of U.S. patent application Ser. No. 13/361,620, filed Jan. 30, 2012, now abandoned, which is a continuation of U.S. patent application Ser. No. 11/368,577, filed Mar. 6, 2006, now U.S. Pat. No. 8,145,317. The entire contents of each of these patent applications are hereby incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for neuromodulation. In some embodiments, the present invention relates to methods and apparatus for achieving bilateral renal neuromodulation.

BACKGROUND

Congestive Heart Failure ("CHF") is a condition that occurs when the heart becomes damaged and reduces blood flow to the organs of the body. If blood flow decreases sufficiently, kidney function becomes altered, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. Moreover, the fluid overload and associated clinical symptoms resulting from these physiologic changes result in additional hospital admissions, poor quality of life and additional costs to the health care system.

In addition to their role in the progression of CHF, the kidneys play a significant role in the progression of Chronic Renal Failure ("CRF"), End-Stage Renal Disease ("ESRD"), hypertension (pathologically high blood pressure) and other cardio-renal diseases. The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys.

It has been established in animal models that the heart failure condition results in abnormally high sympathetic activation of the kidneys. An increase in renal sympathetic nerve activity leads to decreased removal of water and sodium from the body, as well as increased renin secretion. Increased renin secretion leads to vasoconstriction of blood vessels supplying the kidneys which causes decreased renal blood flow. Reduction of sympathetic renal nerve activity, e.g., via denervation, may reverse these processes.

Applicants have previously described methods and apparatus for treating renal disorders by applying a pulsed electric field to neural fibers that contribute to renal function. See, for example, Applicants' co-pending U.S. patent application Ser. No. 11/129,765, filed on May 13, 2005, and Ser. No. 11/189,563, filed on Jul. 25, 2005, both of which are incorporated herein by reference in their entireties. A pulsed electric field ("PEF") may initiate renal neuromodulation, e.g., denervation, for example, via irreversible electroporation or via electrofusion. The PEF may be delivered from apparatus positioned intravascularly, extravascularly, intrato-extravascularly or a combination thereof. Additional methods and apparatus for achieving renal neuromodulation, e.g., via localized drug delivery (such as by a drug pump or infusion catheter) or via use of a stimulation electric field, etc, are described, for example, in co-owned and co-pending U.S. patent application Ser. No. 10/408,665, filed Apr. 8, 2003, and U.S. Pat. No. 6,978,174, both of which are incorporated herein by reference in their entireties.

As used herein, electrofusion comprises fusion of neighboring cells induced by exposure to an electric field. Contact between target neighboring cells for the purposes of electrofusion may be achieved in a variety of ways, including, for example, via dielectrophoresis. In tissue, the target cells may already be in contact, thus facilitating electrofusion.

As used herein, electroporation and electropermeabilization are methods of manipulating the cell membrane or intracellular apparatus. For example, the porosity of a cell membrane may be increased by inducing a sufficient voltage across the cell membrane through, e.g., short, high-voltage pulses. The extent of porosity in the cell membrane (e.g., size and number of pores) and the duration of effect (e.g., temporary or permanent) are a function of multiple variables, such as field strength, pulse width, duty cycle, electric field orientation, cell type or size and/or other parameters.

Cell membrane pores will generally close spontaneously upon termination of relatively lower strength electric fields or relatively shorter pulse widths (herein defined as "reversible electroporation"). However, each cell or cell type has a critical threshold above which pores do not close such that pore formation is no longer reversible; this result is defined as "irreversible electroporation," "irreversible breakdown" or "irreversible damage." At this point, the cell membrane ruptures and/or irreversible chemical imbalances caused by the high porosity occur. Such high porosity can be the result of a single large hole and/or a plurality of smaller holes.

A potential challenge of using intravascular PEF systems for treating renal disorders is to selectively electroporate target cells without affecting other cells. For example, it may be desirable to irreversibly electroporate renal nerve cells that travel along or in proximity to renal vasculature, but it may not be desirable to damage the smooth muscle cells of which the vasculature is composed. As a result, an overly aggressive course of PEF therapy may persistently injure the renal vasculature, but an overly conservative course of PEF therapy may not achieve the desired renal neuromodulation.

Applicants have previously described methods and apparatus for monitoring tissue impedance or conductivity to determine the effects of pulsed electric field therapy, e.g., to determine an extent of electroporation and/or its degree of irreversibility. See, for example, Applicant's co-pending U.S. patent application Ser. No. 11/233,814, filed Sep. 23, 2005, which is incorporated herein by reference in its entirety. Pulsed electric field electroporation of tissue causes a decrease in tissue impedance and an increase in tissue conductivity. If induced electroporation is reversible, tissue impedance and conductivity should approximate baseline levels upon cessation of the pulsed electric field. However, if electroporation is irreversible, impedance and conductivity changes should persist after terminating the pulsed electric field. Thus, monitoring the impedance or conductivity of target and/or non-target tissue may be utilized to determine the onset of electroporation and to determine the type or extent of electroporation. Furthermore, monitoring data may be used in one or more manual or automatic feedback loops to control the electroporation.

It would be desirable to provide methods and apparatus for achieving bilateral renal neuromodulation.

SUMMARY

The present invention provides methods and apparatus for neuromodulation, e.g., via a pulsed electric field ("PEF"), via a stimulation electric field, via localized drug delivery, via high frequency ultrasound, via thermal techniques, combinations thereof, etc. Such neuromodulation may, for example, effectuate irreversible electroporation or electrofusion, necrosis and/or inducement of apoptosis, alteration of gene expression, action potential blockade or attenuation, changes in cytokine up-regulation and other conditions in target neural fibers. In some patients, when the neuromodulatory methods and apparatus of the present invention are applied to renal nerves and/or other neural fibers that contribute to renal neural functions, applicants believe that the neuromodulatory effects induced by the neuromodulation might result in increased urine output, decreased plasma renin levels, decreased tissue (e.g., kidney) and/or urine catecholamines (e.g., norepinephrine), increased urinary sodium excretion, and/or controlled blood pressure. Furthermore, applicants believe that these or other changes might prevent or treat congestive heart failure, hypertension, acute myocardial infarction, end-stage renal disease, contrast nephropathy, other renal system diseases, and/or other renal or cardio-renal anomalies. The methods and apparatus described herein could be used to modulate efferent or afferent nerve signals, as well as combinations of efferent and afferent nerve signals.

Renal neuromodulation preferably is performed in a bilateral fashion, such that neural fibers contributing to renal function of both the right and left kidneys are modulated. Bilateral renal neuromodulation may provide enhanced therapeutic effect in some patients as compared to renal neuromodulation performed unilaterally, i.e., as compared to renal neuromodulation performed on neural tissue innervating a single kidney. In some embodiments, concurrent modulation of neural fibers that contribute to both right and left renal function may be achieved. In additional or alternative embodiments, such modulation of the right and left neural fibers may be sequential. Bilateral renal neuromodulation may be continuous or intermittent, as desired.

When utilizing an electric field, the electric field parameters may be altered and combined in any combination, as desired. Such parameters can include, but are not limited to, voltage, field strength, pulse width, pulse duration, the shape of the pulse, the number of pulses and/or the interval between pulses (e.g., duty cycle), etc. For example, when utilizing a pulsed electric field, suitable field strengths can be up to about 10,000 V/cm and suitable pulse widths can be up to about 1 second. Suitable shapes of the pulse waveform include, for example, AC waveforms, sinusoidal waves, cosine waves, combinations of sine and cosine waves, DC waveforms, DC-shifted AC waveforms, RF waveforms, square waves, trapezoidal waves, exponentially-decaying waves, or combinations. The field includes at least one pulse, and in many applications the field includes a plurality of pulses. Suitable pulse intervals include, for example, intervals less than about 10 seconds. These parameters are provided as suitable examples and in no way should be considered limiting.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which.

DETAILED DESCRIPTION

A. Overview

The present invention relates to methods and apparatus for neuromodulation, e.g., denervation. In some embodiments, the present invention provides methods and apparatus for achieving bilateral renal neuromodulation. Bilateral renal neuromodulation may provide enhanced therapeutic effect in some patients as compared to renal neuromodulation performed unilaterally, i.e., as compared to renal neuromodulation performed on neural tissue innervating a single kidney. In some embodiments, concurrent modulation of neural fibers that contribute to both right and left renal function may be achieved. In additional or alternative embodiments, such modulation of the right and left neural fibers may be sequential. Bilateral renal neuromodulation may be continuous or intermittent, as desired.

The methods and apparatus of the present invention may be used to modulate neural fibers that contribute to renal function and may exploit any suitable neuromodulatory techniques that will achieve the desired neuromodulation. For example, any suitable electrical signal or field parameters, e.g., any electric field that will achieve the desired neuromodulation (e.g., electroporative effect) may be utilized. Alternatively or additionally, neuromodulation may be achieved via localized delivery of a neuromodulatory agent or drug. To better understand the structures of devices of the present invention and the methods of using such devices for bilateral renal neuromodulation, it is instructive to examine the renal anatomy in humans.

B. Selected Embodiments of Methods for Neuromodulation

Figure 1:
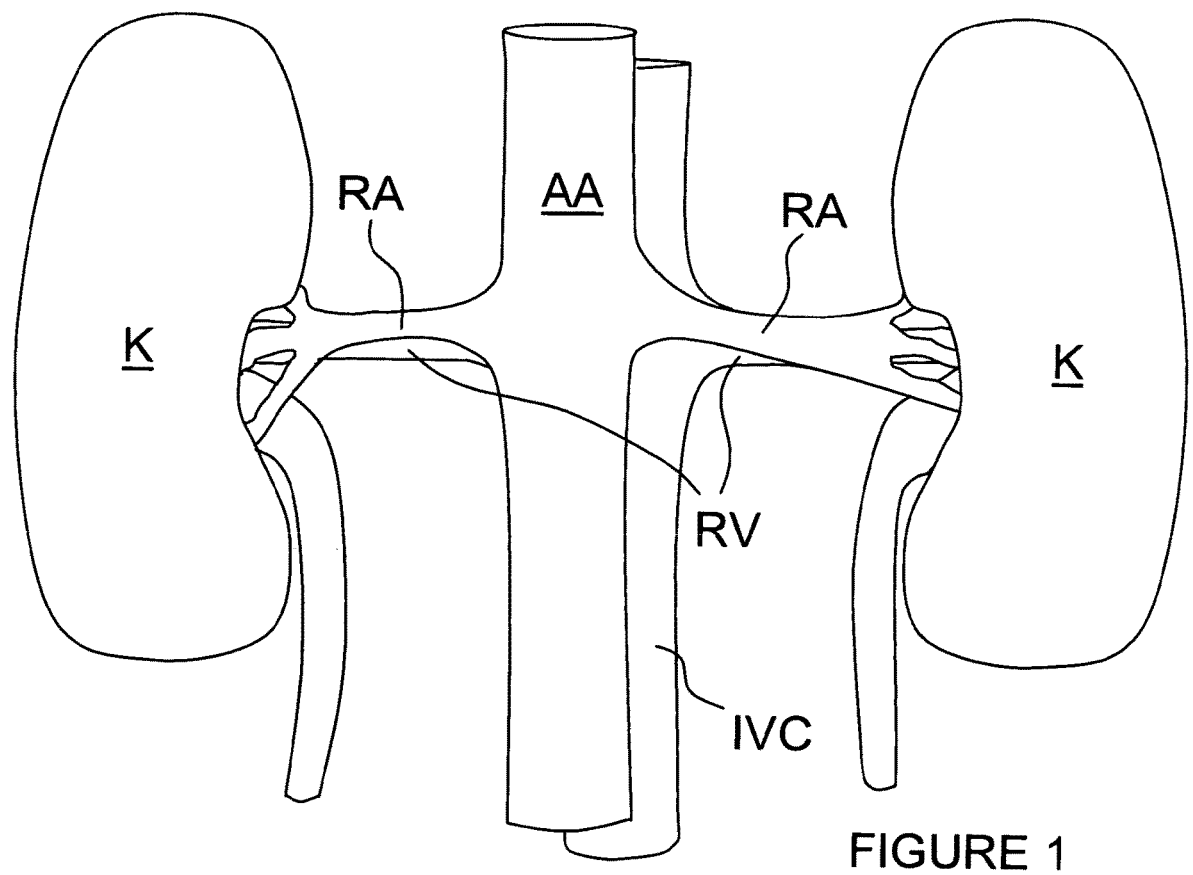
FIG. 1 is a schematic view illustrating human renal anatomy.
Figure 2:
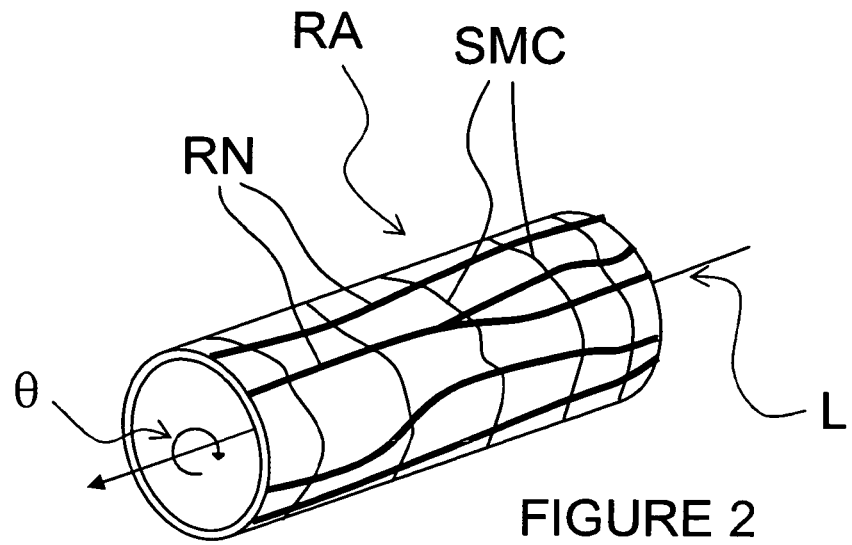
FIG. 2 is a schematic isometric detail view showing the location of the renal nerves relative to the renal artery.

With reference now to FIG. 1, the human renal anatomy includes kidneys K that are supplied with oxygenated blood by renal arteries RA, which are connected to the heart by the abdominal aorta AA. Deoxygenated blood flows from the kidneys to the heart via renal veins RV and the inferior vena cava IVC. FIG. 2 illustrates a portion of the renal anatomy in greater detail. More specifically, the renal anatomy also includes renal nerves RN extending longitudinally along the lengthwise dimension L of renal artery RA generally within the adventitia of the artery. The renal artery RA has smooth muscle cells SMC that surround the arterial circumference and spiral around the angular axis θ of the artery. The smooth muscle cells of the renal artery accordingly have a lengthwise or longer dimension extending transverse (i.e., non-parallel) to the lengthwise dimension of the renal artery. The misalignment of the lengthwise dimensions of the renal nerves and the smooth muscle cells is defined as "cellular misalignment."

Figure 3A:
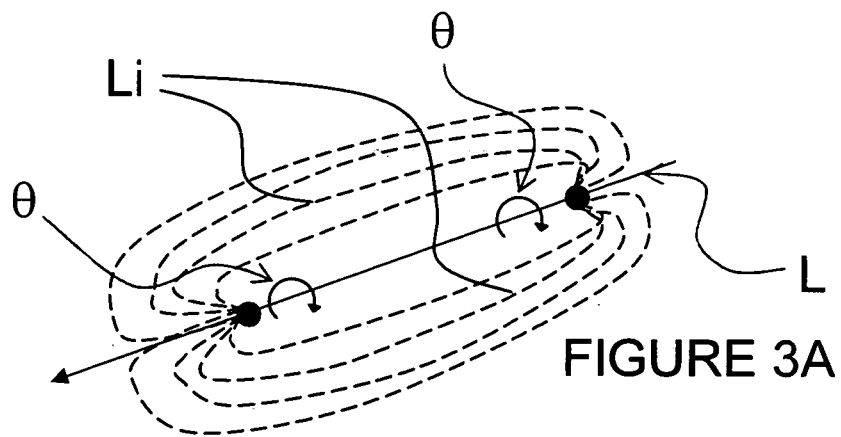
FIGS. 3A and 3B are schematic isometric and end views, respectively, illustrating orienting of an electric field for selectively affecting renal nerves.
Figure 3B:
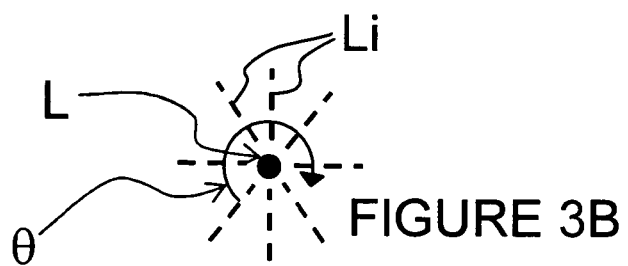

Referring to FIGS. 3A and 3B, the cellular misalignment of the renal nerves and the smooth muscle cells may be exploited to selectively affect renal nerve cells with reduced effect on smooth muscle cells. More specifically, because larger cells require a lower electric field strength to exceed the cell membrane irreversibility threshold voltage or energy for irreversible electroporation, embodiments of electrodes of the present invention may be configured to align at least a portion of an electric field generated by the electrodes with or near the longer dimensions of the cells to be affected. In specific embodiments, the device has electrodes configured to create an electrical field aligned with or near the lengthwise dimension L of the renal artery RA to affect renal nerves RN. By aligning an electric field so that the field preferentially aligns with the lengthwise aspect of the cell rather than the diametric or radial aspect of the cell, lower field strengths may be used to affect target neural cells, e.g., to necrose or fuse the target cells, to induce apoptosis, to alter gene expression, to attenuate or block action potentials, to change cytokine up-regulation and/or to induce other suitable processes. This is expected to reduce total energy delivered to the system and to mitigate effects on non-target cells in the electric field.

Similarly, the lengthwise or longer dimensions of tissues overlying or underlying the target nerve are orthogonal or otherwise off-axis (e.g., transverse) with respect to the longer dimensions of the nerve cells. Thus, in addition to aligning a pulsed electric field ("PEF") with the lengthwise or longer dimensions of the target cells, the PEF may propagate along the lateral or shorter dimensions of the non-target cells (i.e., such that the PEF propagates at least partially out of alignment with non-target smooth muscle cells SMC). Therefore, as seen in FIGS. 3A and 3B, applying a PEF with propagation lines Li generally aligned with the longitudinal dimension L of the renal artery RA is expected to preferentially cause electroporation (e.g., irreversible electroporation), electrofusion or other neuromodulation in cells of the target renal nerves RN without unduly affecting the non-target arterial smooth muscle cells SMC. The pulsed electric field may propagate in a single plane along the longitudinal axis of the renal artery, or may propagate in the longitudinal direction along any angular segment θ through a range of 0°-360°.

A PEF system placed within and/or in proximity to the wall of the renal artery may propagate an electric field having a longitudinal portion that is aligned to run with the longitudinal dimension of the artery in the region of the renal nerves RN and the smooth muscle cells SMC of the vessel wall so that the wall of the artery remains at least substantially intact while the outer nerve cells are destroyed, fused or otherwise affected. Monitoring elements may be utilized to assess an extent of, e.g., electroporation, induced in renal nerves and/or in smooth muscle cells, as well as to adjust PEF parameters to achieve a desired effect.

C. Exemplary Embodiments of Systems and Additional Methods for Neuromodulation

Figure 4:
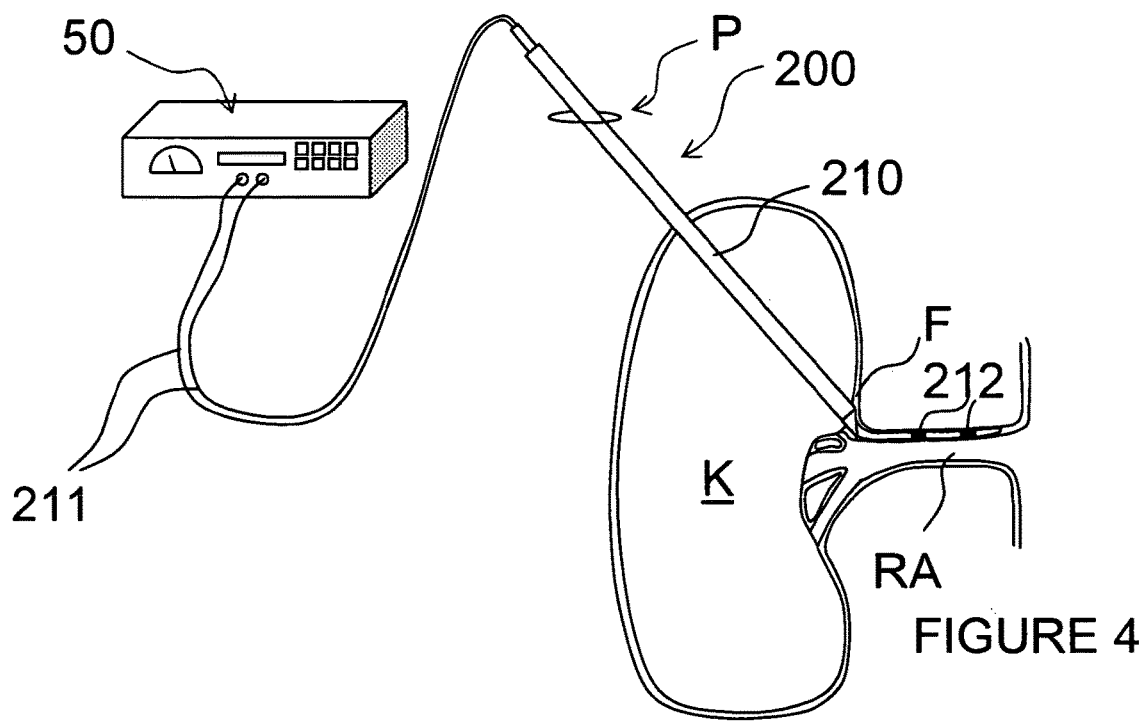
FIG. 4 is a schematic side view, partially in section, illustrating an example of an extravascular method and apparatus for renal neuromodulation.

With reference to FIGS. 4 and 5, examples of PEF systems and methods are described. FIG. 4 shows one embodiment of an extravascular pulsed electric field apparatus 200 that includes one or more electrodes configured to deliver a pulsed electric field to renal neural fibers to achieve renal neuromodulation. The apparatus of FIG. 4 is configured for temporary extravascular placement; however, it should be understood that partially or completely implantable extravascular apparatus additionally or alternatively may be utilized. Applicants have previously described extravascular PEF systems, for example, in co-pending U.S. patent application Ser. No. 11/189,563, filed Jul. 25, 2005, which has been incorporated herein by reference in its entirety.

In FIG. 4, apparatus 200 comprises a laparoscopic or percutaneous PEF system having a probe 210 configured for insertion in proximity to the track of the renal neural supply along the renal artery or vein or hilum and/or within Gerota's fascia under, e.g., CT or radiographic guidance. At least one electrode 212 is configured for delivery through the probe 210 to a treatment site for delivery of pulsed electric field therapy. The electrode(s) 212, for example, may be mounted on a catheter and electrically coupled to a pulse generator 50 via wires 211. In an alternative embodiment, a distal section of the probe 210 may have one electrode 212, and the probe may have an electrical connector to couple the probe to the pulse generator 50 for delivering a PEF to the electrode(s) 212.

The pulsed electric field generator 50 is located external to the patient. The generator, as well as any of the PEF-delivery electrode embodiments described herein, may be utilized with any embodiment of the present invention for delivery of a PEF with desired field parameters. It should be understood that PEF-delivery electrodes of embodiments described hereinafter may be electrically connected to the generator even though the generator is not explicitly shown or described with each embodiment.

The electrode(s) 212 can be individual electrodes that are electrically independent of each other, a segmented electrode with commonly connected contacts, or a continuous electrode. A segmented electrode may, for example, be formed by providing a slotted tube fitted onto the electrode, or by electrically connecting a series of individual electrodes. Individual electrodes or groups of electrodes 212 may be configured to provide a bipolar signal. The electrodes 212 may be dynamically assignable to facilitate monopolar and/or bipolar energy delivery between any of the electrodes and/or between any of the electrodes and an external ground pad. Such a ground pad may, for example, be attached externally to the patient's skin, e.g., to the patient's leg or flank. In FIG. 4, the electrodes 212 comprise a bipolar electrode pair. The probe 210 and the electrodes 212 may be similar to the standard needle or trocar-type used clinically for pulsed RF nerve block. Alternatively, the apparatus 200 may comprise a flexible and/or custom-designed probe for the renal application described herein.

In FIG. 4, the percutaneous probe 210 has been advanced through a percutaneous access site P into proximity with a patient's renal artery RA. The probe pierces the patient's Gerota's fascia F, and the electrodes 212 are advanced into position through the probe and along the annular space between the patient's artery and fascia. Once properly positioned, pulsed electric field therapy may be applied to target neural fibers across the bipolar electrodes 212. Such PEF therapy may, for example, at least partially denervate the kidney innervated by the target neural fibers through irreversible electroporation of cells of the target neural fibers. The electrodes 212 optionally also may be used to monitor the electroporative effects of the PEF therapy. After treatment, the apparatus 200 may be removed from the patient to conclude the procedure.

Figure 5A:
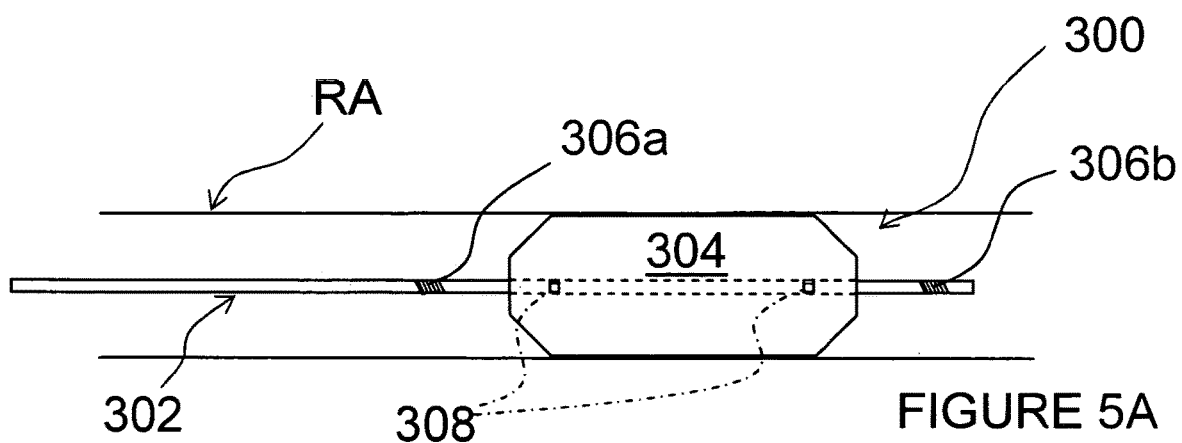
FIGS. 5A and 5B are schematic side views, partially in section, illustrating examples of, respectively, intravascular and intra-to-extravascular methods and apparatus for renal neuromodulation.

Referring now to FIG. 5A, an embodiment of an intravascular PEF system is described. Applicants have previously described intravascular PEF systems, for example, in co-pending U.S. patent application Ser. No. 11/129,765, filed May 13, 2005, which has been incorporated herein by reference in its entirety. The embodiment of FIG. 5A includes an apparatus 300 comprising a catheter 302 having a centering element 304 (e.g., a balloon, an expandable wire basket, other mechanical expanders, etc.), shaft electrodes 306a and 306b disposed along the shaft of the catheter, and optional radiopaque markers 308 disposed along the shaft of the catheter in the region of the centering element 304. The electrodes 306a-b, for example, can be arranged such that the electrode 306a is near a proximal end of the centering element 304 and the electrode 306b is near the distal end of the centering element 304. The electrodes 306 are electrically coupled to the pulse generator 50 (see FIG. 4), which is disposed external to the patient, for delivery of the PEF therapy.

The centering element 304 may comprise an impedance-altering element that alters the impedance between electrodes 306a and 306b during the PEF therapy, for example, to better direct the PEF therapy across the vessel wall. This may reduce an applied voltage required to achieve desired renal neuromodulation. Applicants have previously described use of an impedance-altering element, for example, in co-pending U.S. patent application Ser. No. 14/266,993, filed Nov. 4, 2005, which is incorporated herein by reference in its entirety. When the centering element 304 comprises an inflatable balloon, the balloon may serve as both the centering element for the electrodes 306 and as an impedance-altering electrical insulator for directing an electric field delivered across the electrodes, e.g., for directing the electric field into or across the vessel wall for modulation of target neural fibers. Electrical insulation provided by the element 304 may reduce the magnitude of applied voltage or other parameters of the pulsed electric field necessary to achieve desired field strength at the target fibers.

The electrodes 306 can be individual electrodes (i.e., independent contacts), a segmented electrode with commonly connected contacts, or a single continuous electrode. Furthermore, the electrodes 306 may be configured to provide a bipolar signal, or the electrodes 306 may be used together or individually in conjunction with a separate patient ground pad for monopolar use. As an alternative or in addition to placement of the electrodes 306 along the central shaft of catheter 302, as in FIG. 5A, the electrodes 306 may be attached to the centering element 304 such that they contact the wall of the renal artery RA. In such a variation, the electrodes may, for example, be affixed to the inside surface, outside surface or at least partially embedded within the wall of the centering element. The electrodes optionally may be used to monitor the effects of PEF therapy, as described hereinafter. As it may be desirable to reduce or minimize physical contact between the PEF-delivery electrodes and the vessel wall during delivery of PEF therapy, e.g., to reduce the potential for injuring the wall, the electrodes 306 may, for example, comprise a first set of electrodes attached to the shaft of the catheter for delivering the PEF therapy, and the device may further include a second set of electrodes optionally attached to the centering element 304 for monitoring the effects of PEF therapy delivered via the electrodes 306.

In use, the catheter 302 may be delivered to the renal artery RA as shown, or it may be delivered to a renal vein or to any other vessel in proximity to neural tissue contributing to renal function, in a low profile delivery configuration, for example, through a guide catheter. Once positioned within the renal vasculature, the optional centering element 304 may be expanded into contact with an interior wall of the vessel. A pulsed electric field then may be generated by the PEF generator 50, transferred through the catheter 302 to the electrodes 306, and delivered via the electrodes 306 across the wall of the artery. The PEF therapy modulates the activity along neural fibers that contribute to renal function, e.g., at least partially denervates the kidney innervated by the neural fibers. This may be achieved, for example, via irreversible electroporation, electrofusion and/or inducement of apoptosis in the nerve cells. In many applications, the electrodes are arranged so that the pulsed electric field is aligned with the longitudinal dimension of the renal artery to facilitate modulation of renal nerves with little effect on non-target smooth muscle cells or other cells.

In addition to extravascular and intravascular PEF systems, intra-to-extravascular PEF systems may be provided having electrode(s) that are delivered to an intravascular position, then at least partially passed through/across the vessel wall to an extravascular position prior to delivery of PEF therapy. Intra-to-extravascular positioning of the electrode(s) may place the electrode(s) in closer proximity to target neural fibers during the PEF therapy compared to fully intravascular positioning of the electrode(s). Applicants have previously described intra-to-extravascular PEF systems, for example, in co-pending U.S. patent application Ser. No. 11/324,188 (hereinafter, "the '188 application"), filed Dec. 29, 2005, which is incorporated herein by reference in its entirety.

Figure 5B:
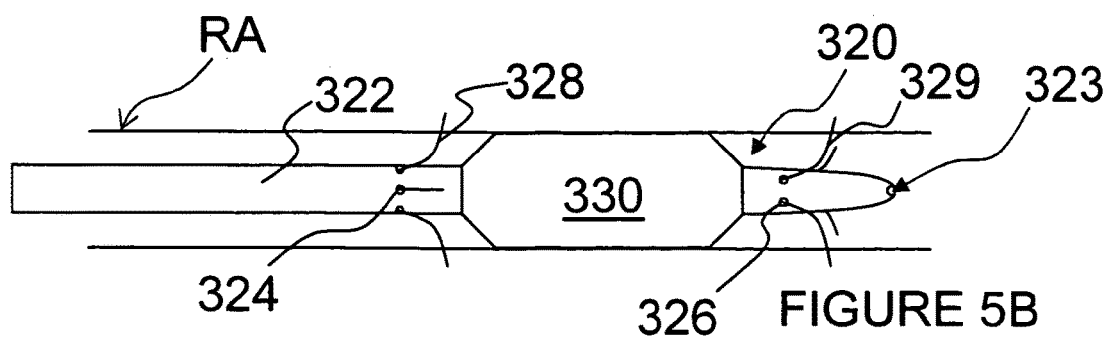

With reference to FIG. 5B, one embodiment of an intra-to-extravascular ("ITEV") PEF system, described previously in the '188 application, is shown. ITEV PEF system 320 comprises a catheter 322 having (a) a plurality of proximal electrode lumens terminating at proximal side-ports 324, (b) a plurality of distal electrode lumens terminating at distal side ports 326, and (c) a guidewire lumen 323. The catheter 322 preferably comprises an equal number of proximal and distal electrode lumens and side ports. The system 320 also includes proximal needle electrodes 328 that may be advanced through the proximal electrode lumens and the proximal side ports 324, as well as distal needle electrodes 329 that may be advanced through the distal electrode lumens and the distal side ports 326.

Catheter 322 comprises an optional expandable centering element 330, which may comprise an inflatable balloon or an expandable basket or cage. In use, the centering element 330 may be expanded prior to deployment of the needle electrodes 328 and 329 in order to center the catheter 322 within the patient's vessel (e.g., within renal artery RA). Centering the catheter 322 is expected to facilitate delivery of all needle electrodes to desired depths within/external to the patient's vessel (e.g., to deliver all of the needle electrodes approximately to the same depth). In FIG. 5B, the illustrated centering element 330 is positioned between the proximal side ports 324 and the distal side ports 326, i.e., between the delivery positions of the proximal and distal electrodes. However, it should be understood that centering element 330 additionally or alternatively may be positioned at a different location or at multiple locations along the length of the catheter 322 (e.g., at a location proximal of the side ports 324 and/or at a location distal of the side ports 326).

As illustrated in FIG. 5B, the catheter 322 may be advanced to a treatment site within the patient's vasculature (e.g., to a treatment site within the patient's renal artery RA) over a guidewire (not shown) via the lumen 323. During intravascular delivery, the electrodes 328 and 329 may be positioned such that their non-insulated and sharpened distal regions are positioned within the proximal and distal lumens, respectively. Once positioned at a treatment site, a medical practitioner may advance the electrodes via their proximal regions that are located external to the patient. Such advancement causes the distal regions of the electrodes 328 and 329 to exit side ports 324 and 326, respectively, and pierce the wall of the patient's vasculature such that the electrodes are positioned extravascularly via an ITEV approach.

The proximal electrodes 328 can be connected to PEF generator 50 as active electrodes and the distal electrodes 329 can serve as return electrodes. In this manner, the proximal and distal electrodes form bipolar electrode pairs that align PEF therapy with a longitudinal axis or direction of the patient's vasculature. As will be apparent, the distal electrodes 329 alternatively may comprise the active electrodes and the proximal electrodes 328 may comprise the return electrodes. Furthermore, the proximal and/or the distal electrodes may comprise both active and return electrodes. Any combination of active and distal electrodes may be utilized, as desired.

When the electrodes 328 and 329 are connected to PEF generator 50 and are positioned extravascularly, and with centering element 330 optionally expanded, PEF therapy may proceed to achieve desired neuromodulation. After completion of the PEF therapy, the electrodes may be retracted within the proximal and distal lumens, and centering element 330 may be collapsed for retrieval. ITEV PEF system 320 then may be removed from the patient to complete the procedure. Additionally or alternatively, the system may be repositioned to provide PEF therapy at another treatment site, for example, to provide bilateral renal neuromodulation.

It is expected that PEF therapy, as well as other methods and apparatus of the present invention for neuromodulation (e.g., stimulation electric fields, localized drug delivery, high frequency ultrasound, thermal techniques, etc.), whether delivered extravascularly, intravascularly, intra-to-extravascularly or a combination thereof, may, for example, effectuate irreversible electroporation or electrofusion, necrosis and/or inducement of apoptosis, alteration of gene expression, action potential blockade or attenuation, changes in cytokine up-regulation and other conditions in target neural fibers. In some patients, when such neuromodulatory methods and apparatus are applied to renal nerves and/or other neural fibers that contribute to renal neural functions, applicants believe that the neuromodulatory effects induced by the neuromodulation might result in increased urine output, decreased plasma renin levels, decreased tissue (e.g., kidney) and/or urine catecholamines (e.g., norepinephrine), increased urinary sodium excretion, and/or controlled blood pressure. Furthermore, applicants believe that these or other changes might prevent or treat congestive heart failure, hypertension, acute myocardial infarction, end-stage renal disease, contrast nephropathy, other renal system diseases, and/or other renal or cardio-renal anomalies for a period of months, potentially up to six months or more. This time period may be sufficient to allow the body to heal; for example, this period may reduce the risk of CHF onset after an acute myocardial infarction, thereby alleviating a need for subsequent re-treatment. Alternatively, as symptoms reoccur, or at regularly scheduled intervals, the patient may return to the physician for a repeat therapy. The methods and apparatus described herein could be used to modulate efferent or afferent nerve signals, as well as combinations of efferent and afferent nerve signals. Neuromodulation in accordance with the present invention preferably is achieved without completely physically severing, i.e., without fully cutting, the target neural fibers. However, it should be understood that such neuromodulation may functionally sever the neural fibers, even though the fibers may not be completely physically severed. Apparatus and methods described herein illustratively are configured for percutaneous use. Such percutaneous use may be endoluminal, laparoscopic, a combination thereof, etc.

The apparatus described above with respect to FIGS. 4 and 5 additionally may be used to quantify the efficacy, extent or cell selectivity of PEF therapy to monitor and/or control the therapy. When a pulsed electric field initiates electroporation, the impedance of the electroporated tissue begins to decrease and the conductivity of the tissue begins to increase. If the electroporation is reversible, the tissue electrical parameters will return or approximate baseline values upon cessation of the PEF. However, if the electroporation is irreversible, the changes in tissue parameters will persist after termination of the PEF. These phenomena may be utilized to monitor both the onset and the effects of PEF therapy. For example, electroporation may be monitored directly using, for example, conductivity measurements or impedance measurements, such as Electrical Impedance Tomography ("EIT") and/or other electrical impedance/conductivity measurements like an electrical impedance or conductivity index. Such electroporation monitoring data optionally may be used in one or more feedback loops to control delivery of PEF therapy.

In order to collect the desired monitoring data, additional monitoring electrodes optionally may be provided in proximity to the monitored tissue. The distance between such monitoring electrodes preferably would be specified prior to therapy delivery and used to determine conductivity from impedance or conductance measurements. For the purposes of the present invention, the imaginary part of impedance may be ignored such that impedance is defined as voltage divided by current, while conductance may be defined as the inverse of impedance (i.e., current divided by voltage), and conductivity may be defined as conductance per unit distance. Applicants have previously described methods and apparatus for monitoring PEF therapy, as well as exemplary PEF waveforms, in co-pending U.S. patent application Ser. No. 11/233,814, filed Sep. 23, 2005, which has been incorporated herein by reference in its entirety.

Although the embodiments of FIGS. 4 and 5 illustratively comprise bipolar apparatus, it should be understood that monopolar apparatus alternatively may be utilized. For example, an active monopolar electrode may be positioned intravascularly, extravascularly or intra-to-extravascularly in proximity to target neural fibers that contribute to renal function. A return electrode ground pad may be attached to the exterior of the patient. Finally, PEF therapy may be delivered between to the in vivo monopolar electrode and the ground pad to effectuate desired renal neuromodulation. Monopolar apparatus additionally may be utilized for bilateral renal neuromodulation.

It may be desirable to achieve bilateral renal neuromodulation. Bilateral neuromodulation may enhance the therapeutic effect in some patients as compared to renal neuromodulation performed unilaterally, i.e., as compared to renal neuromodulation performed on neural tissue innervating a single kidney. For example, bilateral renal neuromodulation may further reduce clinical symptoms of CHF, hypertension, acute myocardial infarction, contrast nephropathy, renal disease and/or other cardio-renal diseases. FIGS. 6A-6H illustrate stages of a method for bilateral renal neuromodulation utilizing the intravascular apparatus of FIG. 5A. However, it should be understood that such bilateral neuromodulation alternatively may be achieved utilizing the extravascular apparatus of FIG. 4, utilizing the intra-to-extravascular apparatus of FIG. 5B, or utilizing any alternative intravascular apparatus, extravascular apparatus, intra-to-extravascular apparatus (including monopolar apparatus) or combination thereof.

Figure 6A:
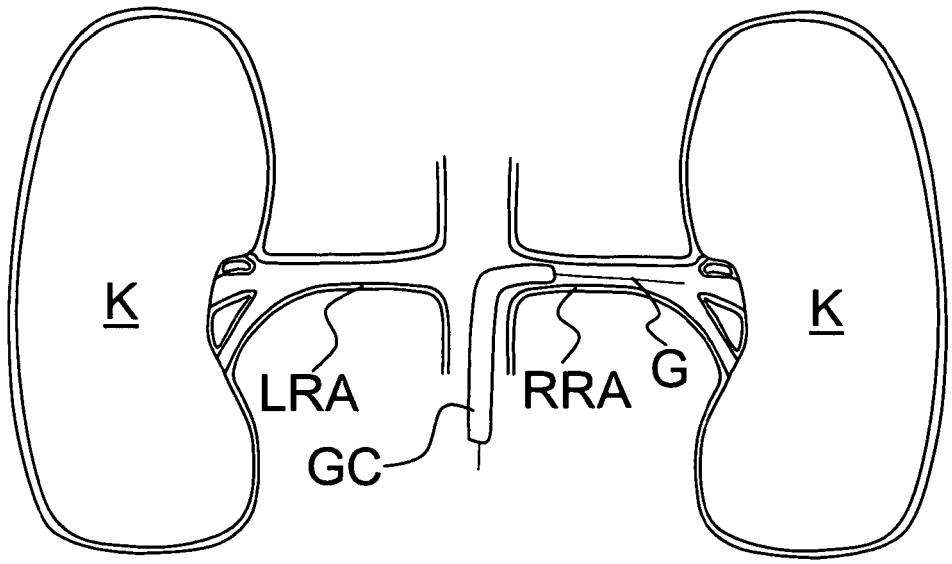
FIGS. 6A-6H are schematic side views, partially in section, illustrating methods of achieving bilateral renal neuromodulation utilizing apparatus of the present invention, illustratively utilizing the apparatus of FIG. 5A.
Figure 6B:
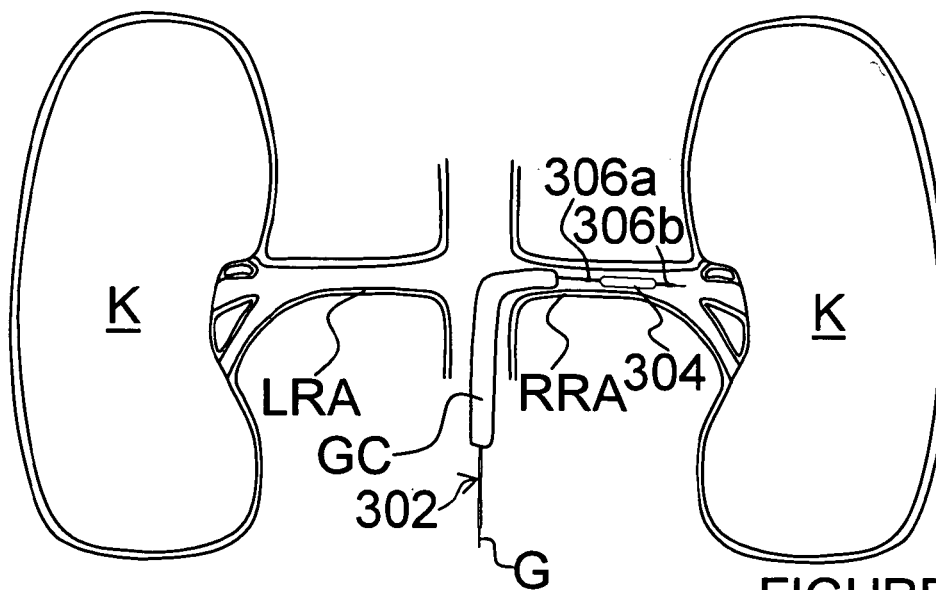
Figure 6C:
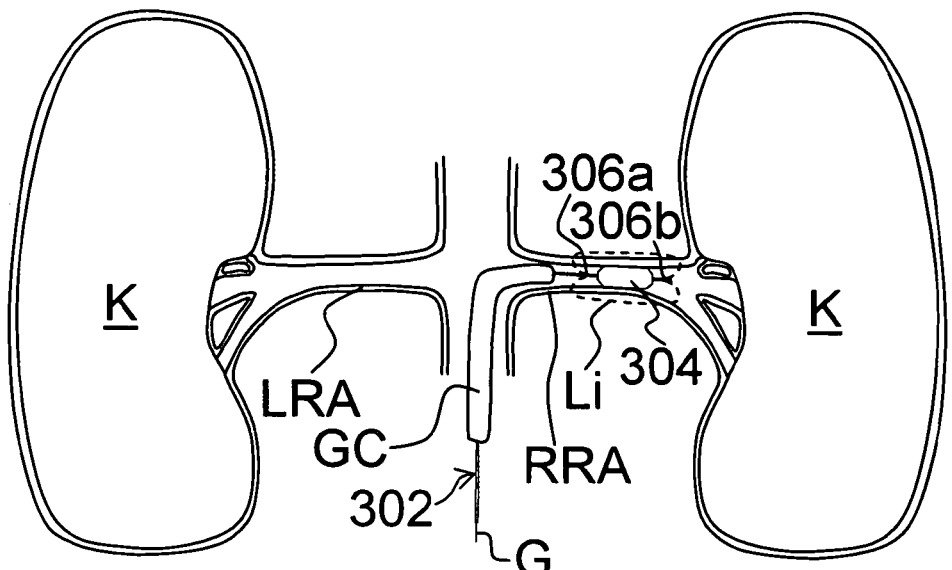
Figure 6D:
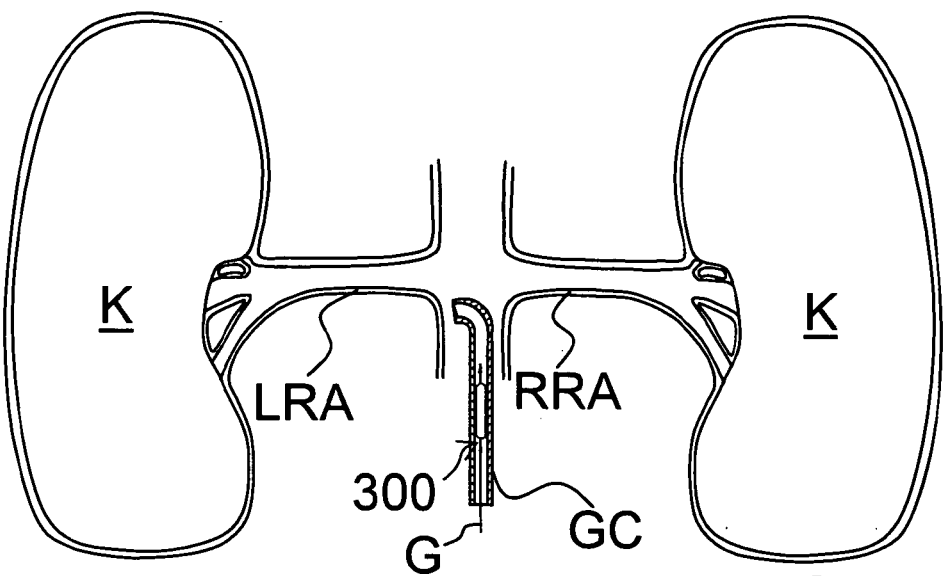
Figure 6E:
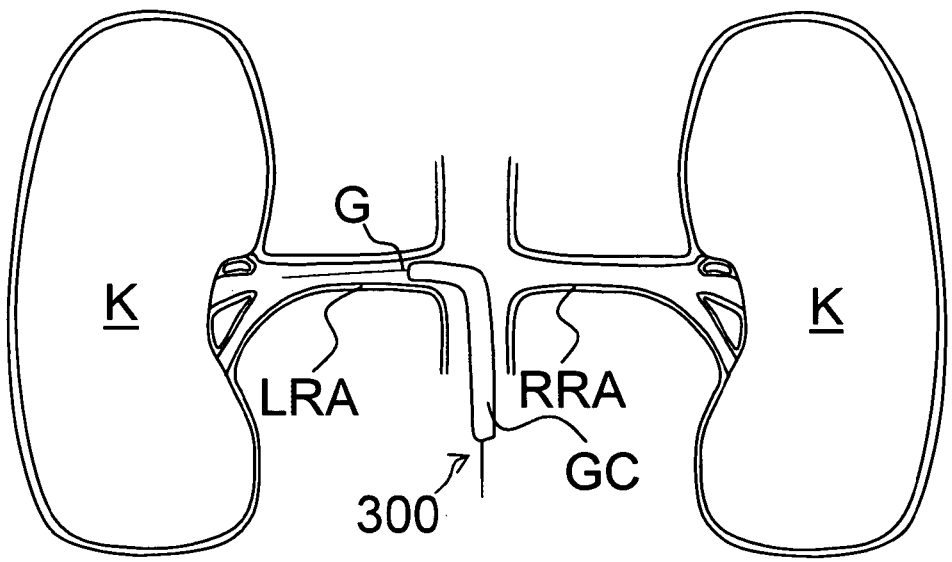

As seen in FIGS. 6A and 6E, a guide catheter GC and a guidewire G may be advanced into position within, or in proximity to, either the patient's left renal artery LRA or right renal artery RRA. In FIG. 6A, the guidewire illustratively has been positioned in the right renal artery RRA, but it should be understood that the order of bilateral renal neuromodulation illustrated in FIGS. 6A-6H alternatively may be reversed. Additionally or alternatively, bilateral renal neuromodulation may be performed concurrently on both right and left neural fibers that contribute to renal function, as in FIGS. 7-9, rather than sequentially, as in FIG. 6.

With the guidewire and the guide catheter positioned in the right renal artery, the catheter 302 of the apparatus 300 may be advanced over the guidewire and through the guide catheter into position within the artery. As seen in FIG. 6B, the optional centering element 304 of the catheter 302 is in a reduced delivery configuration during delivery of the catheter to the renal artery. In FIG. 6C, once the catheter is properly positioned for PEF therapy, the element 304 optionally may be expanded into contact with the vessel wall, and the guidewire G may be retracted from the treatment zone, e.g., may be removed from the patient or may be positioned more proximally within the patient's aorta.

Expansion of element 304 may center the electrodes 306 within the vessel and/or may alter impedance between the electrodes. With apparatus 300 positioned and deployed as desired, PEF therapy may be delivered in a bipolar fashion across the electrodes 306 to achieve renal neuromodulation in neural fibers that contribute to right renal function, e.g., to at least partially achieve renal denervation of the right kidney. As illustrated by propagation lines Li, the pulsed electric field may be aligned with a longitudinal dimension of the renal artery RA and may pass across the vessel wall. The alignment and propagation path of the pulsed electric field is expected to preferentially modulate cells of the target renal nerves without unduly affecting non-target arterial smooth muscle cells.

As seen in FIG. 6D, after completion of the PEF therapy, the element 304 may be collapsed back to the reduced delivery profile, and the catheter 302 may be retracted from the right renal artery RRA, for example, to a position in the guide catheter GC within the patient's abdominal aorta. Likewise, the guide catheter GC may be retracted to a position within the patient's aorta. The retracted guide catheter may be repositioned, e.g., rotated, such that its distal outlet is generally aligned with the left renal artery LRA. The guidewire G then may be re-advanced through the catheter 302 and the guide catheter GC to a position within the left renal artery LRA, as shown in FIG. 6E (as will be apparent, the order of advancement of the guidewire and the guide catheter optionally may be reversed when accessing either renal artery).

Figure 6F:
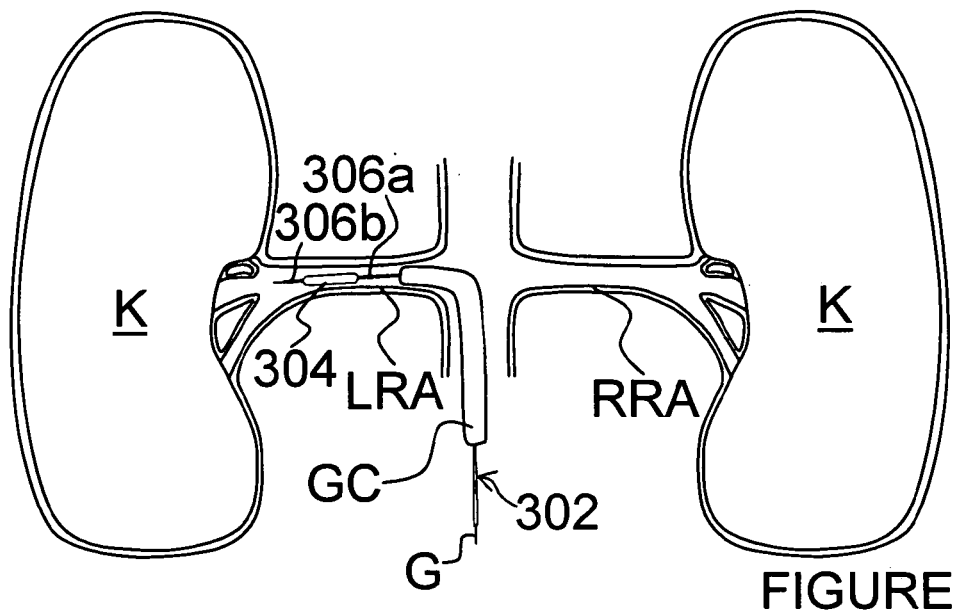
Figure 6G:
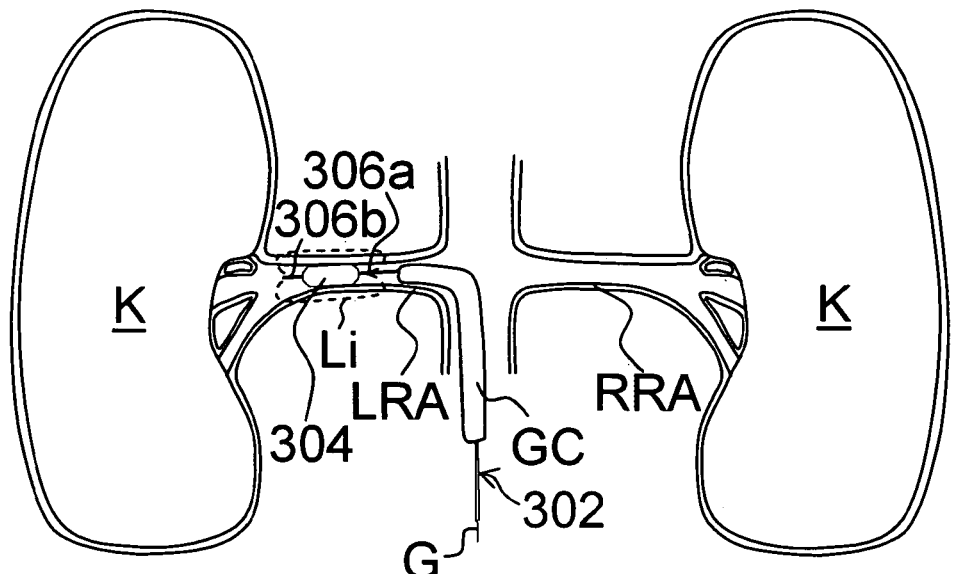
Figure 6H:
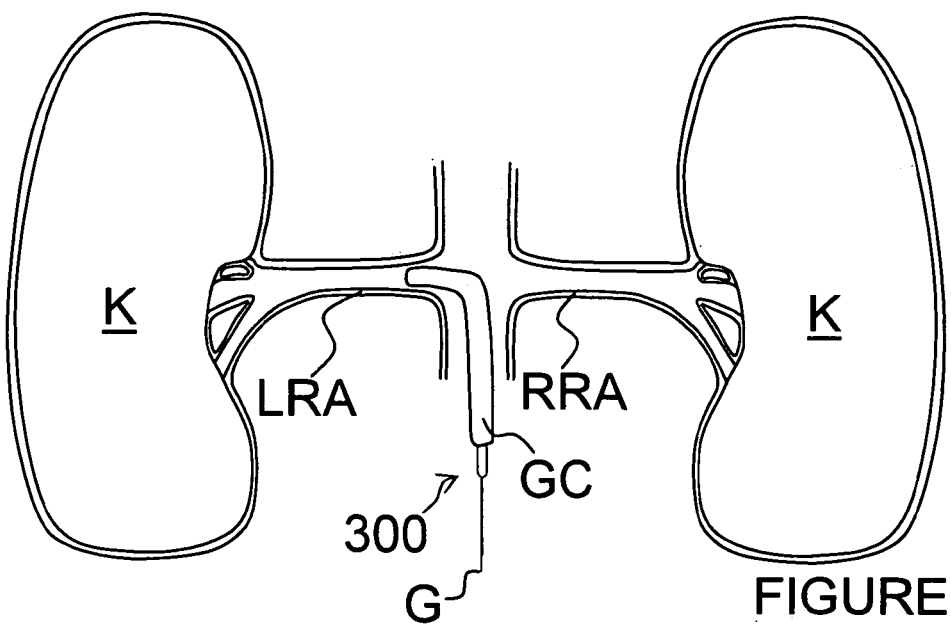

Next, the catheter 302 may be re-advanced over the guidewire and through the guide catheter into position within the left renal artery, as shown in FIG. 6F. In FIG. 6G, once the catheter is properly positioned for PEF therapy, the element 304 optionally may be expanded into contact with the vessel wall, and the guidewire G may be retracted to a position proximal of the treatment site. PEF therapy then may be delivered in a bipolar fashion across the electrodes 306, for example, along propagation lines Li, to achieve renal neuromodulation in neural fibers that contribute to left renal function, e.g., to at least partially achieve renal denervation of the left kidney. As seen in FIG. 6H, after completion of the bilateral PEF therapy, the element 304 may be collapsed back to the reduced delivery profile, and the catheter 302, as well as the guidewire G and the guide catheter GC, may be removed from the patient to complete the bilateral renal neuromodulation procedure.

Figure 7A:
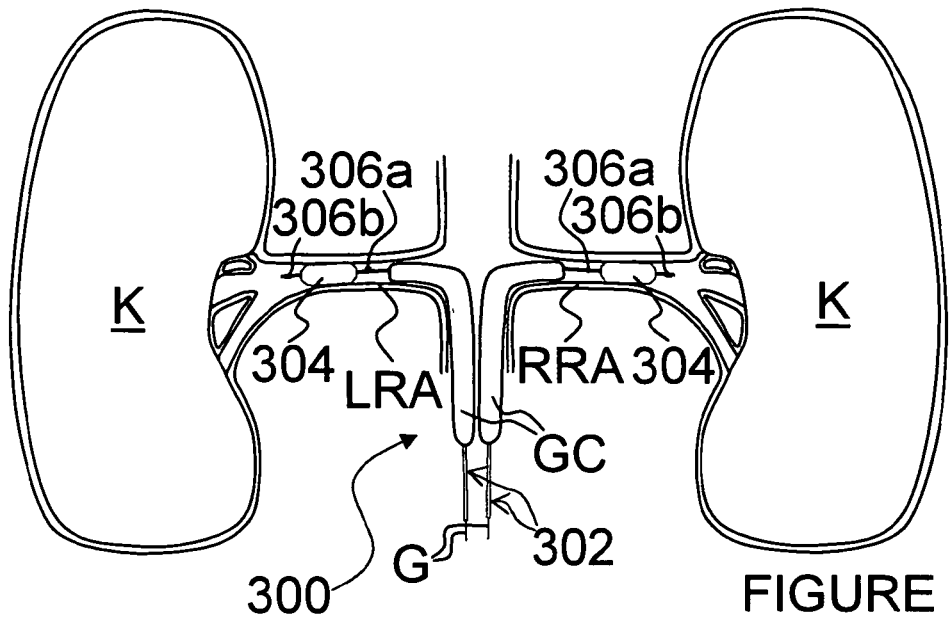
FIGS. 7A and 7B are schematic side views, partially in section, illustrating methods of achieving concurrent bilateral renal neuromodulation utilizing embodiments of the apparatus of FIG. 5A.
Figure 7B:
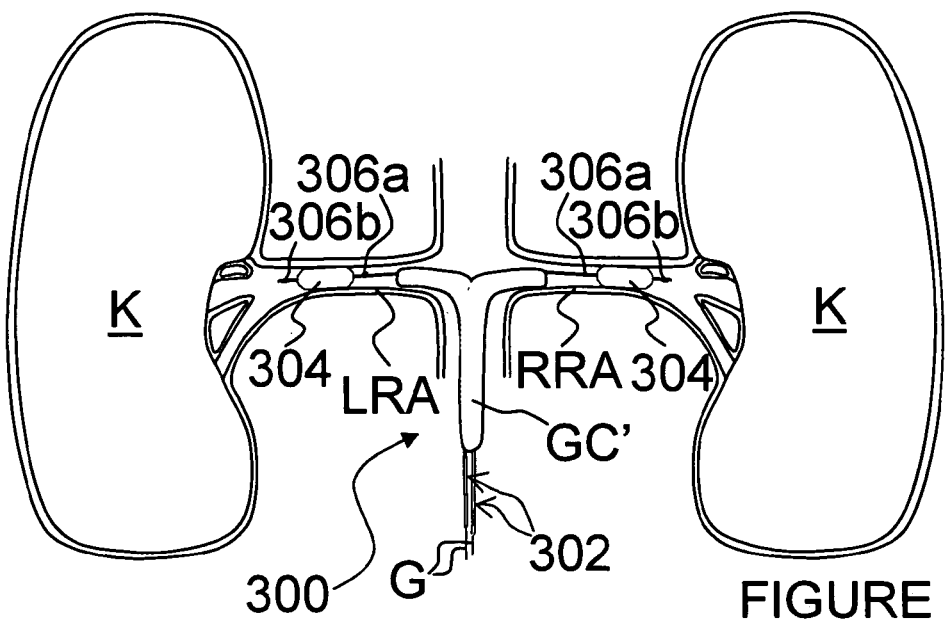

As discussed previously, bilateral renal neuromodulation optionally may be performed concurrently on fibers that contribute to both right and left renal function. FIGS. 7A and 7B illustrate embodiments of apparatus 300 for performing concurrent bilateral renal neuromodulation. In the embodiment of FIG. 7A, apparatus 300 comprises dual PEF therapy catheters 302, as well as dual guidewires G and guide catheters GC. One catheter 302 is positioned within the right renal artery RRA, and the other catheter 302 is positioned within the left renal artery LRA. With catheters 302 positioned in both the right and left renal arteries, PEF therapy may be delivered concurrently by the catheters 302 to achieve concurrent bilateral renal neuromodulation, illustratively via an intravascular approach.

In one example, separate arteriotomy sites may be made in the patient's right and left femoral arteries for percutaneous delivery of the two catheters 302. Alternatively, both catheters 302 may be delivered through a single femoral access site, either through dual guide catheters or through a single guide catheter. FIG. 7B illustrates an example of apparatus 300 for concurrent bilateral renal neuromodulation utilizing a single arteriotomy access site. In the example of FIG. 7B, both catheters 302 are delivered through a custom bifurcated guide catheter GC' having a bifurcated distal region for concurrently delivering the catheters 302 to the right and left renal arteries. Concurrent (or sequential) bilateral PEF therapy then may proceed.

Figure 8:
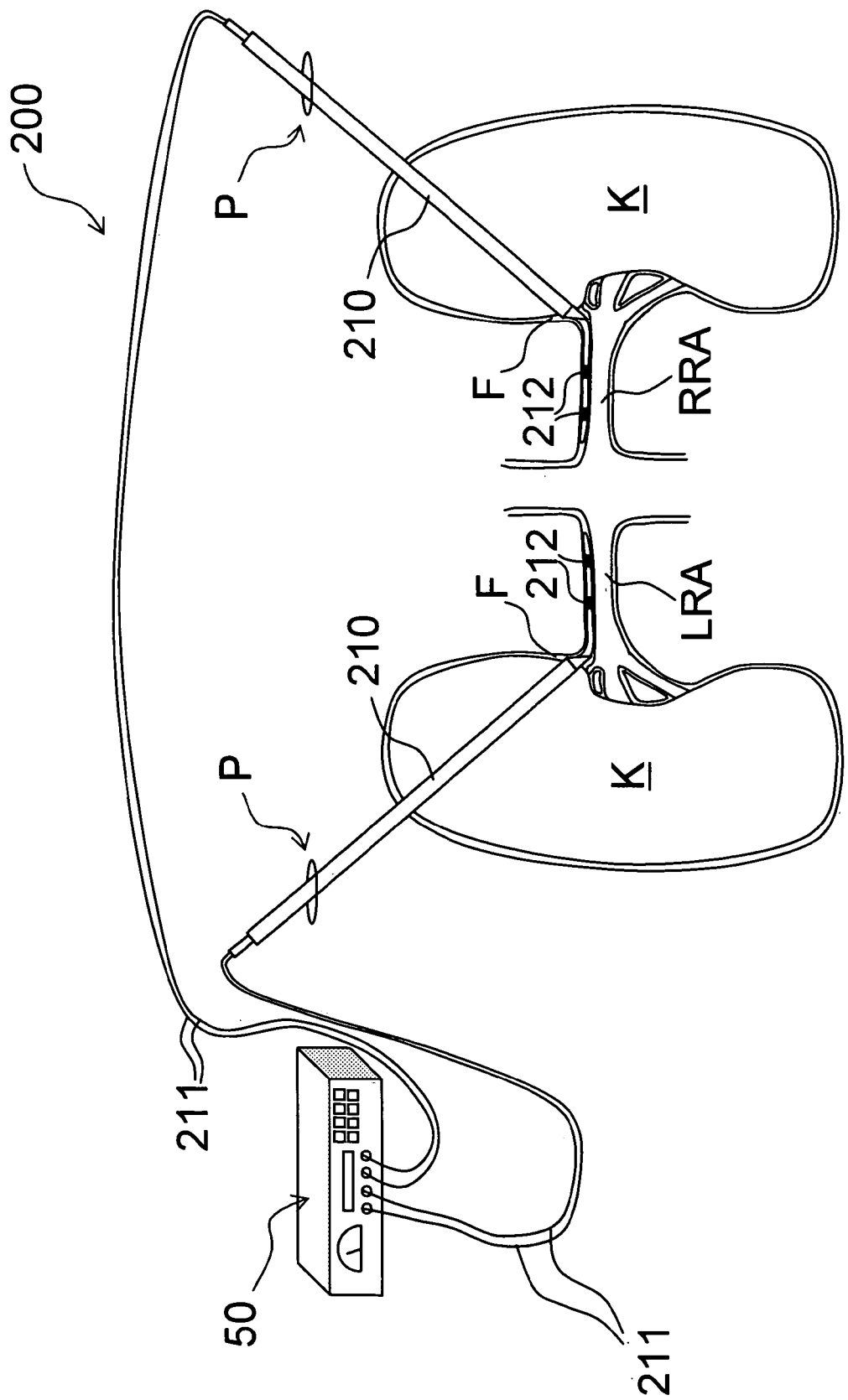
FIG. 8 is a schematic side view, partially in section, illustrating methods of achieving concurrent bilateral renal neuromodulation utilizing an alternative embodiment of the apparatus of FIG. 4.

FIG. 8 illustrates additional methods and apparatus for concurrent bilateral renal neuromodulation. In FIG. 8, an embodiment of extravascular apparatus 200 comprising dual probes 210 and electrodes 212. The electrodes have been positioned in the vicinity of both the left renal artery LRA and the right renal artery RRA. PEF therapy may be delivered concurrently by the electrodes 212 to achieve concurrent bilateral renal neuromodulation, illustratively via an extravascular approach.

As will be apparent, intra-to-extravascular apparatus alternatively may be utilized for bilateral renal neuromodulation. Such bilateral renal neuromodulation may be performed sequentially, concurrently or a combination thereof. For example, ITEV PEF system 320 of FIG. 5B may be utilized for bilateral renal neuromodulation.

Additional methods and apparatus for achieving renal neuromodulation, e.g., via localized drug delivery (such as by a drug pump or infusion catheter) or via use of a stimulation electric field, etc, also may utilized. Examples of such methods and apparatus have been described previously, for example, in co-owned and co-pending U.S. patent application Ser. No. 10/408,665, filed Apr. 8, 2003, and in U.S. Pat. No. 6,978,174, both of which have been incorporated herein by reference in their entireties.

Figure 9:
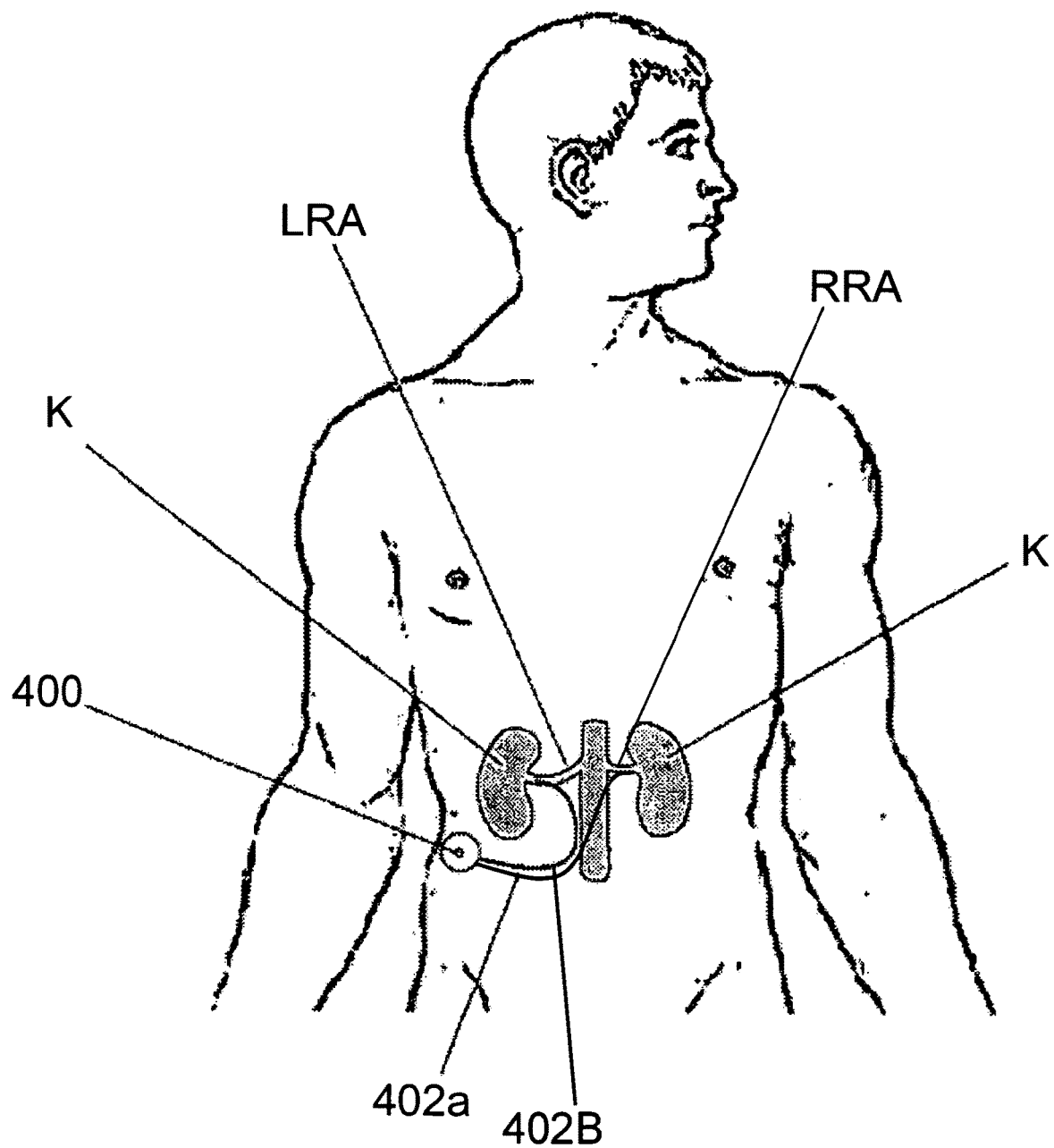
FIG. 9 is a schematic view illustrating an example of methods and apparatus for achieving bilateral renal neuromodulation via localized drug delivery.

FIG. 9 shows one example of methods and apparatus for achieving bilateral renal neuromodulation via localized drug delivery. In FIG. 9, drug reservoir 400, illustratively an implantable drug pump, has been implanted within the patient. Drug delivery catheters 402a and 402b are connected to the drug reservoir and extend to the vicinity of the right renal artery RRA and the left renal artery LRA, respectively, for delivery of one or more neuromodulatory agents or drugs capable of modulating neural fibers that contribute renal function. Delivering the agent(s) through catheters 402a and 402b may achieve bilateral renal neuromodulation. Such drug delivery through catheters 402a and 402b may be conducted concurrently or sequentially, as well as continuously or intermittently, as desired, in order to provide concurrent or sequential, continuous or intermittent, renal neuromodulation, respectively.

In an alternative embodiment of the apparatus of FIG. 9, catheters 402a and 402b may only temporarily be positioned at a desired location, e.g., for acute delivery of the neuromodulatory agent(s) from an external drug reservoir, such as a syringe. Such temporary positioning may comprise, for example, intravascular, extravascular and/or intra-to-extravascular placement of the catheters. In another alternative embodiment, the drug reservoir 400 may be replaced with an implantable neurostimulator or a pacemaker-type device, and catheters 402 may be replaced with electrical leads coupled to the neurostimulator for delivery of an electric field, such as a pulsed electric field or a stimulation electric field, to the target neural fibers. In yet another alternative embodiment, electrical techniques may be combined with delivery of neuromodulatory agent(s) to achieve desired bilateral renal neuromodulation.

Although preferred illustrative variations of the present invention are described above, it will be apparent to those skilled in the art that various changes and modifications may be made thereto without departing from the invention. For example, although the variations primarily have been described for use in combination with pulsed electric fields, it should be understood that any other electric field may be delivered as desired, including stimulation or nerve block electric fields, and any other alternative neuromodulatory techniques, such as localized delivery of a neuromodulatory agent or drug, may be utilized. It is intended in the appended claims to cover all such changes and modifications that fall within the true spirit and scope of the invention.

We claim:

1. A method comprising:
    intravascularly advancing a catheter comprising a neuromodulation element through a guide catheter and over a guidewire to a first position within a first renal artery associated with a first kidney of a patient;
    modulating a function of a first renal nerve adjacent to the first renal artery using the neuromodulation element;
    retracting the catheter into the guide catheter;
    repositioning the guide catheter and the guidewire into a second renal artery associated with a second kidney of the patient;
    re-advancing the catheter through the guide catheter and over the guidewire to a second position within the second renal artery; and
    modulating a function of a second renal nerve adjacent to the second renal artery using the neuromodulation element.

2. The method of claim 1, wherein repositioning the guide catheter and guidewire comprises rotating the guide catheter to orient a distal portion of the guide catheter toward the second renal artery.

3. The method of claim 2, wherein the distal portion of the guide catheter comprises a pre-formed shape.

4. The method of claim 1, further comprising, after intravascularly advancing the catheter through the guide catheter and over the guidewire to the first position within the first renal artery and before modulating the function of the first renal nerve, expanding a centering element into contact with a wall of the first renal artery.

5. The method of claim 4, wherein the centering element comprises at least one of a balloon or an expandable wire basket.

6. The method of claim 4, further comprising, after modulating the function of the first renal nerve and before retracting the catheter into the guide catheter, collapsing the centering element to a reduced delivery profile.

7. The method of claim 1, further comprising, after re-advancing the catheter through the guide catheter and over the guidewire to the second position within the second renal artery and before modulating the function of the second renal nerve, expanding a centering element into contact with a wall of the second renal artery.

8. The method of claim 7, wherein the centering element comprises at least one of a balloon or an expandable wire basket.

9. The method of claim 1, further comprising, prior to re-advancing the catheter through the guide catheter and over the guidewire to the second position within the second renal artery, re-advancing the guidewire through the guide catheter to the second renal artery.

10. The method of claim 1, wherein retracting the catheter into the guide catheter comprises retracting the catheter and the guidewire into the guide catheter.

11. The method of claim 1, further comprising, after intravascularly advancing the catheter through the guide catheter and over the guidewire to the first position within the first renal artery and before modulating the function of the first renal nerve, retracting the guidewire into the guide catheter.

12. The method of claim 1, further comprising, after re-advancing the catheter through the guide catheter and over the guidewire to the second position within the second renal artery and before modulating the function of the second renal nerve, retracting the guidewire into the guide catheter.

13. The method of claim 1, wherein modulating the function of the first renal nerve comprises delivering a drug to the first renal nerve via the neuromodulation element.

14. The method of claim 1, wherein modulating the function of the first renal nerve comprises delivering ultrasound to the first renal nerve via the neuromodulation element.

15. The method of claim 1, wherein modulating the function of the first renal nerve comprises delivering a pulsed electric field to the first renal nerve via the neuromodulation element.

16. The method of claim 1, wherein modulating the function of the first renal nerve comprises delivering thermal energy to the first renal nerve via the neuromodulation element.

17. The method of claim 1, wherein modulating the function of the first renal nerve comprises delivering a stimulation electric field to the first renal nerve via the neuromodulation element.

18. The method of claim 1, wherein modulating the function of the first renal nerve comprises delivering a radio frequency waveform to the first renal nerve via the neuromodulation element.

19. A method comprising:

intravascularly advancing a catheter comprising a neuromodulation element through a guide catheter and over a guidewire to a first position within a first renal artery associated with a first kidney of a patient, wherein the catheter comprises a neuromodulation element;

modulating a function of a first renal nerve adjacent to the first renal artery by at least delivering a drug, ultrasound, a pulsed electric field, thermal energy, electrical stimulation, or a radio frequency waveform to the first renal nerve via the neuromodulation element;

after modulating the function of the first renal nerve, retracting the catheter into the guide catheter;

after retracting the catheter into the guide catheter, repositioning the guidewire into a second renal artery associated with a second kidney of the patient;

repositioning the guide catheter into the second renal artery, wherein repositioning the guide catheter comprises rotating the guide catheter to orient a distal portion of the guide catheter toward the second renal artery;

re-advancing the catheter through the guide catheter and over the guidewire to a second position within the second renal artery; and modulating a function of a second renal nerve adjacent to the second renal artery using the neuromodulation element.

* * * * *